| United States Patent [19] | [11] Patent Number: 4,923,885 |
| Hupe et al. | [45] Date of Patent: May 8, 1990 |

[54] 5-AMINO-1-(4-NAPHTHOYLBENZYL)-1,2,3-TRIAZOLE-4-CARBOXAMIDES AND ANALOGS AS ANTIPROLIFERATIVE AGENTS

[75] Inventors: Donald Hupe, Westfield; Matthew J. Wyvratt, Mountainside, both of N.J.

[73] Assignee: Merck & Co., Inc., Rahway, N.J.

[21] Appl. No.: 233,779

[22] Filed: Aug. 19, 1988

[51] Int. Cl.$^5$ ............................................. C07D 213/04
[52] U.S. Cl. ........................................ 514/359; 548/255
[58] Field of Search ......................... 548/255; 514/359

[56] References Cited

U.S. PATENT DOCUMENTS 4,227,004  10/1980  Wildonger .......................... 548/255
4,590,201  5/1986  Bochis et al. ........................ 548/255

FOREIGN PATENT DOCUMENTS 151528  8/1985  European Pat. Off. ............ 548/255

OTHER PUBLICATIONS

M. Bosma et al., J. Cellular Physiology, vol. 135, 317–323 (1988).
M. Berridge, Biotechnology, pp. 541–546, Jun. 1984.
M. Berridge, Scientific American, vol. 254, pp. 142–152 (1985).
E. Carofoli et al., Scientific American, vol. 263, pp. 70–78 (1985).

*Primary Examiner*—Richard L. Raymond
*Assistant Examiner*—Raymond Covington
*Attorney, Agent, or Firm*—Curtis C. Panzer; Robert J. North; Joseph F. DiPrima

[57] ABSTRACT

Novel 5-Amino-1-(4-Naphthoylbenzyl)-1,2,3-triazole-4-carboxamides and analogs are disclosed as having antiproliferative activities useful in the treatment and control of psoriasis, inflammatory bowel syndrome, cutaneous leishmanilisis and certain types of cancer.

8 Claims, No Drawings

5-AMINO-1-(4-NAPHTHOYLBENZYL)-1,2,3-TRIAZOLE-4-CARBOXAMIDES AND ANALOGS AS ANTIPROLIFERATIVE AGENTS

A. BACKGROUND OF THE INVENTION

5-Amino-1-(4-benzoyl-benzyl)-1,2,3-triazole-4-carboxamides have been known as anticoccidial agents. As such the compounds and the preparations thereof were disclosed in the U.S. Pat. No. 4,590,201 issued on May 20, 1986 to Richard J. Bochis, John C. Chabala and Michael H. Fisher.

Psoriasis is a chronic skin disease which is characterized by hyperproliferation of the epidermis as well as by focal accumulations of lymphocytic cells. Cell cycle estimates in psoriasis suggest that the average germinative psoriatic cell divides every 37 hours compared to 152 hours in normal skin, and the role of hyperproliferation in the production of lesions is evidenced by the fact that antiprolifelitive agents such as methotrexate are presently used therapeutically for symptomatic treatment of the disease. Other chemotherapeutic agents which have been used experimentally with success in clearing lesions include similar antimetabolites which disrupt nucleotide metabolism and thereby inhibit proliferation such as mycophenolic acid or thioguanine.

As disclosed in a copending application U.S. Ser. No. 87,494 filed Aug. 31, 1987, we found that these known 5-amino-1-(4-benzoylbenzyl)-1,2,3-triazole4-carboxamides are effective antiproliferative agents potentially effective in the treatment and management of psoriasis, inflammatory bowel syndrome, cutaneous leishmanilisis, and certain types of cancer that involved the transportation of individual cells to other tissues from a metastasizing tumor. In addition, we found that the novel compounds of the present invention are unexpectedly more (up to 10-fold) active than the known compounds.

Accordingly, it is the object of this invention to provide a new class of compounds for treating and managing psoriasis, inflammatory bowel syndrome, cutaneous leishmanilisis and certain types of cancer. It is also the object of this invention to provide pharmaceutical compositions and methods of treatment using the novel compounds as the active ingredients.

B. DETAILED DESCRIPTION OF THE INVENTION

This invention relates to a novel class of compounds of formula:

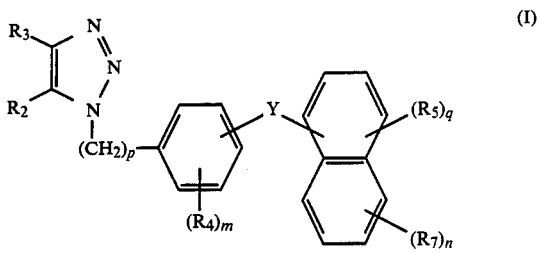

wherein p is 0 to 2; m and n independently are 0 to 4; and q is 0 to 3; Y is O, S, SO, $SO_2$, CO, CHCN, $CH_2$, CHF or C=$NR_6$ where $R_6$ is hydrogen, loweralkyl, hydroxy, loweralkoxy, amino loweralkylamino, diloweralkylamino or cyano; and, $R_4$, $R_5$ and $R_7$ independently are halogen, cyano, trifluoromethyl, loweralkanoyl, nitro, loweralkyl, loweralkoxy, carboxy, carbalkoxy, trifluoromethoxy, acetamido, loweralkylthio, loweralkylsulfonyl, loweralkylsulfonyl, trichlorovinyl, trifluoromethylthio, trifluoromethylsulfinyl, or trifluoromethylsulfonyl;

$R_2$ is amino, mono or diloweralkyl amino, acetamido, acetimido, ureido, formamido, formimido or guanidino; and $R_3$ is carbamoyl, cyano, carbazoyl, amidino or N-hydroxycarbamoyl.

The term "lower" referred to above represents straight or branch $C_{1-20}$ preferably $C_{1-6}$. For example, the expression "loweralkyl" means $C_{1-20}$ alkyl preferably $C_{1-6}$ alkyl such as methyl, ethyl, i-propyl, t-butyl, pentyl and hexyl.

The preferred compounds for the new methods are of formula (I) wherein:

p is 1; Y is O, S, CO or CH2;

$R_4$ is fluoro, chloro, bromo, methyl, trifluoromethyl, cyano, carbomethoxy, trifluoromethoxy, trifluoromethylthio, or trichlorovinyl;

$R_5$ and $R_7$ independently are halogen, methyl, trifluoromethyl, cyano, carbalkoxy, nitro, trichlorovinyl, trifluoromethoxy, or trifluoromethylthio;

$R_2$ is amino;

$R_3$ is carbamoyl (—$CONH_2$); and m, n and q independently are 0, 1 or 2.

The most preferred compounds for the new methods are of formulae (I) wherein p is 1;

$R_4$ is halogen especially chloro or fluoro;

m is 0, 1 or 2;

n and q independently are 0 or 1; and $R_5$ and $R_7$ independently are halogen especially chloro.

C. THE PREPARATION OF THE COMPOUNDS FOR THE PRESENT INVENTION

The compounds to be used in this invention can be prepared by the procedures described in the U.S. Pat. No. 4,590,201. These preparations are hereby incorporated by reference as part of this Application.

The compounds may be prepared, for example, by the methods outlined below:

Scheme I

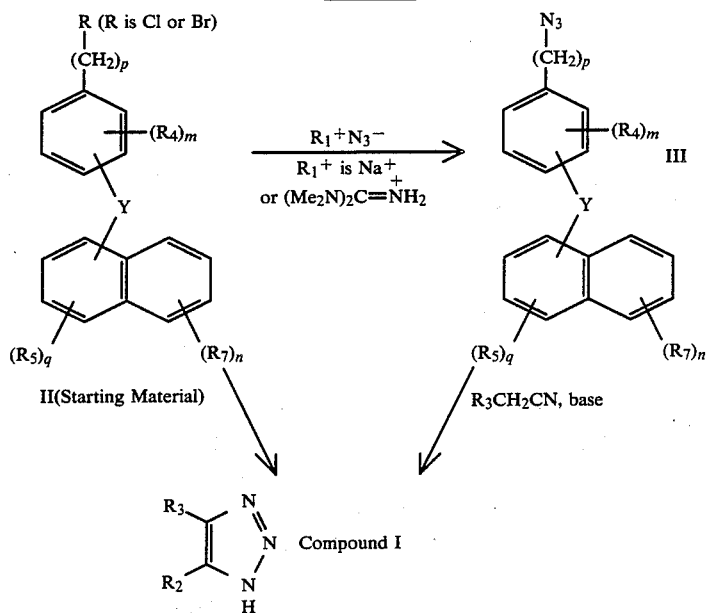

The reaction of converting (III) to Compound (I) is carried out in solvents such as aromatic hydrocarbons, lower alkanols, dimethylformamide, dimethylsulfoxide or hexamethylphosphortriamide. The base may be any alkali metal or alkaline earth hydroxide, alkoxide or hydride such as sodium ethoxide, potassium t-butoxide, magnesium ethoxide, sodium hydroxide, sodium hydride, or potassium carbonate chosen to be compatible with the reaction solvent. Generally the reaction is conducted at from −40° C. to 100° C. and is complete in from 15 min. to 48 h. The product of the reaction is isolated by techniques known to those skilled in the art.

As shown in Scheme II below, the starting materials used for the preparation of the instant compounds are prepared using techniques known to those skilled in the art. A procedure for the preparation of the starting materials wherein Y is a carbonyl or methylene, involves a lithiation reaction of a benzene wherein a substituent of halogen or methoxy is ortho to the position of attachment of the benzoyl moiety and a methyl or substituted silyloxy is present.

The reaction is carried out using an organolithium reagent such as n-butyllithium in an inert solvent at temperatures of from 0° to −80° C. The lithiation reaction is substantially complete in from 30 minutes to 4 hours. The lithiated intermediate is allowed to react in situ with an acylating agent such as a substituted naphthoyl chloride, naphthoate ester, or nitrile. This phase of the reaction is conducted at from −80° to 25° C. and is complete in from 15 minutes to 6 hours. The product is isolated using known techniques.

SCHEME II

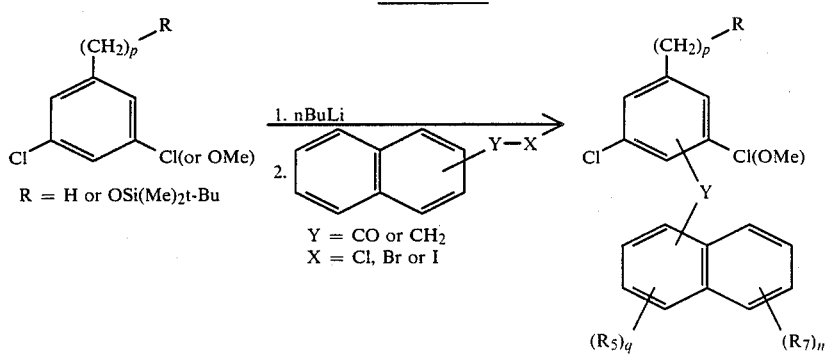

SCHEME II

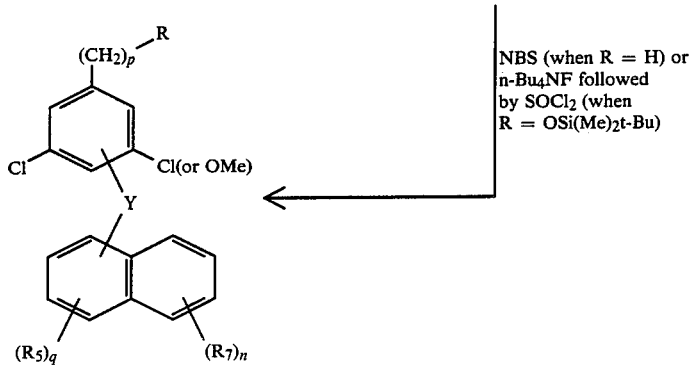

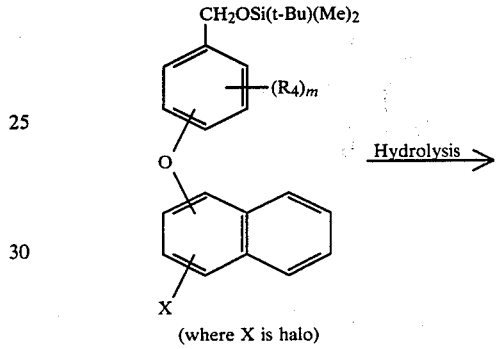

The preparation of the starting materials wherein Y is O involves the coupling of an appropriately substituted phenol and a naphthyl halide, for example,

SCHEME III

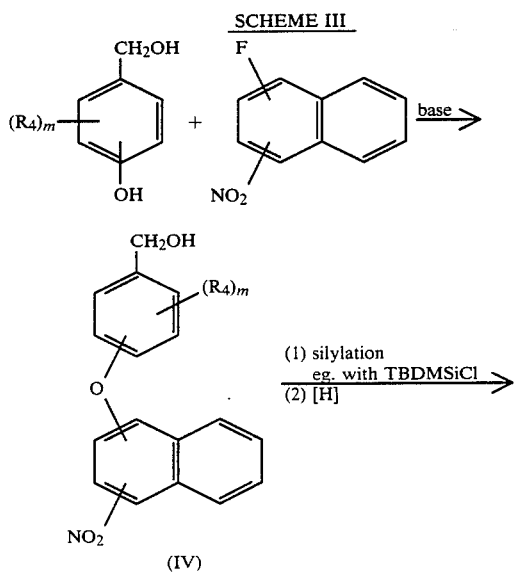

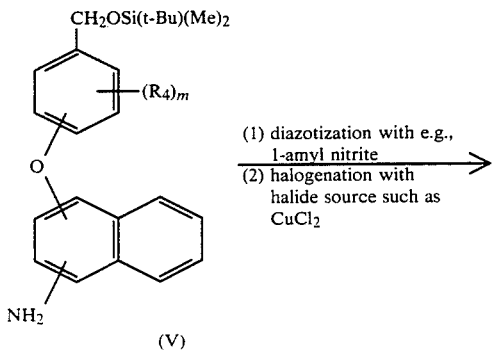

-continued
SCHEME III

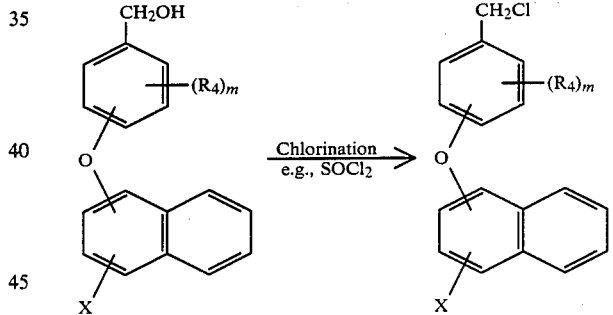

Wherein TBDMSiCl is

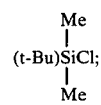

and t-Bu is t-butyl and Me is methyl.

D. UTILITY OF THE PRESENT INVENTION

This invention relates to a method of treatment for patients suffering from psoriasis, inflammatory bowel syndrome, cutaneous leishmaniasis, leukemia or related types of cancer which involves the administration of a compound of formula (I) as the active constituent.

For the treatment of these conditions and diseases a compound of formula (I) may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparation. Tablets containing the active ingredient in admixture with non-toxic pharmaceutically acceptable excipients may also be manufactured by known methods. The excipients used may be for example, (1) inert diluents such as calcium carbonate, lactose, calcium phosphate or sodium phosphate; (2) granulating and disintegrating agents such as corn starch, or alginic acid; (3) binding agents such as starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,160,452; and 4,265,874 to form osmotic therapeutic tablets for controlled release. In some cases, formulations for oral use may be in the form of hard gelatin capsules wherein the active ingredient is mixed with an inert solid diluent, for example, calcium carbonate, calcium phosphate or kaolin. They may also be in the form of soft gelatin capsules wherein the active ingredient is mixed with water or an oil medium, for example peanut oil, liquid paraffin, or olive oil.

Aqueous suspensions normally contain the active materials in admixture with excipients suitable for the manufacture of aqueous suspensions. Such excipients may be (1) suspending agents such as sodium carboxymethylcellulose, methylcellulose, hydroxypropylmethylcellulose, sodium alqinate, polyvinylpyrrolidone, gum tragacanth and gum acacia;

(2) dispersing or wetting agents which may be
 (a) a naturally-occurring phosphatide such as lecithin,
 (b) a condensation product of an alkylene oxide with a fatty acid, for example, polyoxyethylene stearate,
 (c) a condensation product of ethylene oxide with a long chain aliphatic alcohol, for example, heptadecaethyleneoxycetanol,
 (d) a condensation product of ethylene oxide with a partial ester derived from a fatty acid and a hexitol such as polyoxyethylene sorbitol monooleate, or
 (e) a condensation product of ethylene oxide with a partial ester derived from a fatty acid and a hexitol anhydride, for example polyoxyethylene sorbitan monooleate.

The aqueous suspensions may also contain one or more preservatives, for example, ethyl or n-propyl p-hydroxybenzoate; one or more coloring agents; one or more flavoring agents; and one or more sweetening agents such as sucrose or saccharin.

Oily suspension may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents and flavoring agents may be added to provide a palatable oral preparation. These compositions may be preserved by the addition of an antioxidant such as ascorbic acid.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example, those sweetening, flavoring and coloring agents described above may also be present.

The pharmaceutical compositions of the invention may also be in the form of oil-in-water emulsions. The oily phase may be a vegetable oil such as olive oil or arachis oils, or a mineral oil such as liquid paraffin or a mixture thereof. Suitable emulsifying agents may be (1) naturally-occurring gums such as gum acacia and gum tragacanth, (2) naturally-occurring phosphatides such as soy bean and lecithin, (3) esters or partial esters derived from fatty acids and hexitol anhydrides, for example, sorbitan monooleate, (4) condensation products of said partial esters with ethylene oxide, for example, polyoxyethylene sorbitan monooleate. The emulsions may also contain sweetening and flavoring agents.

Syrups and elixirs may be formulated with sweetening agents, for example, glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to known methods using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectibles.

A compound of formula (I) may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the active compounds are employed.

The amount of active ingredient that may be combined with the carrier materials to produce a single dosage form will vary depending upon the host treated and the particular mode of administration. For example, a formulation intended for the oral administration of humans may contain from 5 mg to 5 gm of active agent compounded with an appropriate and convenient amount of carrier material which may vary from about 5 to about 95 percent of the total composition. Dosage unit forms will generally contain between from about 25 mg to about 500 mg of active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

E. BIOLOGICAL EVIDENCE IN SUPPORT OF UTILITY OF THE COMPOUNDS WITHIN THE SCOPE OF THE INVENTION

It has been found that the compounds of formula (I) have antiproliferative activities. It has been demonstrated that specific inhibitors of nucleotide biosynthesis can cure psoriasis, tumor formation and other proliferative disorders. For example, Mycophenolic acid, a specific inhibitor of guanine nucleotide production, controls psoriasis by causing remission when given orally, albeit with unacceptable side effects. Other specific inhibitors of purine or pyrimidine nucleotide biosynthesis, including methotrexate, fluorouracil, thioguanine and N-phosphonacetyl-L-aspartate have been shown to be effective in treating the disease, although each has unacceptable side effects due to toxicity. It is apparent, however, that those drugs that regulate the rate of proliferation of cells by inhibiting nucleotide biosynthesis should also demonstrate efficacy in psoriasis and other proliferative disorders.

In vitro experiments were carried out which demonstrated the efficacy of amino-1,2,3-triazoles, for example, 5-amino-1-(4-(4-chloronaphthoyl)-3,5-dichlorobenzyl)-1,2, 3-triazole-4-carboxamide (Compound A) at 0.08 g/ml in inhibiting nucleotide biosynthesis in normal human epidermal keratinocyte cells. It has been known that it is the hyperproliferation of these cells in humans which causes psoriasis.

As shown in Table 1, levels of drug ranging from approximately 0.08 to 1.0 μ/ml show substantial inhibition of growth of Normal Human Epidermal Keratinocytes (NHEK). In these experiments, NHEK's were cultured in Dulbecco's modified Eagle's medium with 10% fetal calf serum at 37° C., 5% $CO_2$. Each well of a 96 well plate was seeded with 2000 cells in 200 μl of each drug dilution in duplicate. A plate was stopped and fixed for each time point, stained with Giemsa and then read in a Titertek plate reader at 650 nm, and the absorbances were calibrated with known cell numbers on control plates. NHEK's were obtained from Clonetics Corporation at the secondary stage.

TABLE 5

Activities of Compound A and analogs in Proliferation Assays vs Normal Human Epidermal Keratinocytes

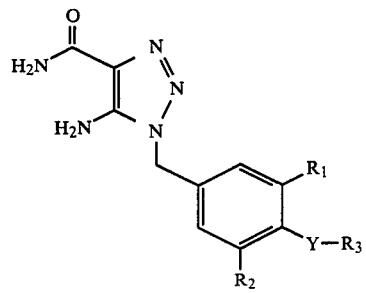

| $R_1$ | $R_2$ | X | $R_3$ | $ED_{50}$ NHEK μg/ml |
|---|---|---|---|---|
| Cl | Cl | C=O | β-Naphth | 1.0 |
| Cl | Cl | C=O | α-Naphth | .3 |
| Cl* | Cl | C=O | α-Naphth-4-Cl | .08 |
| Cl | Cl | $CH_2$ | α-Naphth-4-Cl | .3 |
| Cl | Cl | O | α-Naphth-4-Cl | .3 |
| Cl** | Cl | C=O | phenyl-4-Cl | .5-1.0 |

Naphth = naphthyl
*Compound A
**Reference compound

EXAMPLE 1

4-(2-Naphthoyl)-3,5-dichlorotoluene

To a cold (−60° C.) stirred solution of 3,5-dichlorotoluene (2.5 g, 15.5 mmol) in 30 ml of dry tetrahydrofuran under a nitrogen atmosphere, a 2.6 M solution of n-butyllithium in hexane (6.3 ml, 16.3 mmol) was added slowly over 15 minutes. The reaction mixture was stirred for an additional 30 minutes at −60° C. and then treated dropwise with a solution of 2-naphthoyl chloride (2.95 g, 15.5 mmol) in 15 ml of dry tetrahydrofuran over 15 minutes. The reaction mixture was stirred for 4 hours at −60° C. and then quenched with 4 ml of saturated $NH_4Cl$ solution. The mixture was permitted to come to room temperature at which point it was diluted with 20 ml of water and 20 ml of ether. The layers were separated and the aqueous layer further extracted with ether. The combined extracts were washed with brine, dried with anhydrous magnesium sulfate and concentrated under reduced pressure to give 4.76 g of crude product. This material was chromatographed on silica gel (20:1 hexane:ethyl acetate) to give 1.71 g of pure product.

EXAMPLE 2

4-(2-Naphthoyl)-3,5-dichlorobenzyl bromide

A solution of 1.56 q (4.95 mmol) of 4-(2-naphthoyl)3,5-dichlorotoluene and 72 mg (0.3 mmol) of dibenzoylperoxide in 50 ml of benzene was heated to near reflux at which point 1.10 mg (6.19 mmol) of N-bromosuccinimide was added. The reaction mixture was stirred at reflux for 19 hours and then concentrated under reduced pressure. The residue was dissolved in methylene chloride:hexane (70:30) and the resulting precipitate was collected by filtration. The filtrate was concentrated to give 2.27 g of crude product which was chromatographed on silica gel (20:1 hexane:ethyl acetate) to give 0.89 q of pure monobromide product.

EXAMPLE 3

4-(2-Naphthoyl)-3,5-dichlorobenzyl azide

A suspension of 4-(2-naphthoyl)-3,5-dichlorobenzyl bromide (0.633 g, 1.61 mmol) and sodium azide (0.245 g, 3.77 mmol) in 10 ml of ethanol was heated at reflux for 3 hours. The reaction mixture was filtered and the precipitate rinsed with ethanol. The filtrate was concentrated and the residue redissolved in ether. The resulting precipitate was collected and washed thoroughly with ether. Concentration afforded 0.594 g of an oil which slowly crystallized. The crude azide was used in the next step without any further purification.

EXAMPLE 4

5-Amino-1-[4-(2-naphthoyl)-3,5-dichlorobenzyl]-1,2,3-triazole-4-carboxamide

A suspension of 2-cyanoacetamide (0.135 g, 1.61 mmol) in 14 ml of ethanol was heated to 60° C. and treated with a 1.49 M methanolic NaOH solution (1.08 ml). The reaction mixture was stirred for 10 minutes and then treated with 0.573 g (1.61 mmol) of 4-(2-naphthoyl)-3,5-dichlorobenzyl azide. This mixture was stirred at 60° C. for two hours and then cooled. Glacial acetic acid (0.92 ml) was added followed by 20 ml of water. This aqueous mixture was extracted with methylene chloride. The combined extracts were dried with anhydrous magnesium sulfate and concentrated to afford 0.555 g of crude triazole which was chromatographed on silica gel (3% methanol/methylene chloride) to give 136 mg of pure product.

EXAMPLE 5

4-(1-Naphthoyl)-3,5-dichlorotoluene

To a stirred, cold (-60° C.) solution of 3,5-dichlorotoluene (3.5 g, 21.7 mmol) in dry tetrahydrofuran (30 ml), 2.6 M n-butyllithium in hexane (8.78 ml, 22.8 mmol) was added dropwise over 15 minutes. The reaction mixture was stirred for one hour at −60° C. and then treated with a solution of 1-naphthoyl chloride (4.14 g, 21.7 mmol) in 15 ml of dry tetrahydrofuran over a period of 15 minutes. The mixture was stirred for 3.5 hours at −60° C. and then quenched with 4.8 ml of saturated NH4Cl solution. The mixture was permitted to warm to room temperature and then diluted with 30 ml of water and 30 ml of ether. The layers were thoroughly mixed and then separated. The etheral layer was backed-washed with brine and dried with anhydrous magnesium sulfate. Concentration afforded 7.12 g of crude product which was chromatographed on silica gel (20:1 hexane:ethyl acetate) to give 1.59 g (23 %).

EXAMPLE 6

4-(1-Naphthoyl)-3.5-dichlorobenzyl bromide A warm solution (60° C.) of 4-(1-naphthoyl)-3,5-dichloro toluene (1.5 g, 4.76 mmol) and dibenzoylperoxide (72 mg, 0.3 mmol) in 50 ml of benzene was treated with N-bromosuccin-imide (1.06 g, 5.95 mmol) and then heated at reflux for 19 hours. The reaction mixture was cooled and then diluted with hexane to precipitate succinimide. The precipitate was collected by filtration and thoroughly washed with 70:30 methylene chloride:ethyl acetate. The filtrate was concentrated to give 2.43 g of crude product. Chromatography on silica gel (20:1 hexane:ethyl acetate) afforded 0.98 g of pure monobromide product.

EXAMPLE 7

5-Amino-1-[4-(1-naphthoyl)-3,5-dichlorobenzyl]-1,2,3-triazole-4-carboxamide

A solution of 5-amino-1,2,3-triazole-4-carboxamide (364 mg, 2.86 mmol) in 5 ml of dry dimethylformamide was treated with 50 % sodium hydride dispersion in mineral oil (137 mg, 2.86 mmol). The reaction mixture was warmed to 45° C. and then stirred for 45 minutes. A solution of 4-(1-naphthoyl)-3,5-dichlorobenzyl bromide (0.98 g, 2.49 mmol) in 5 ml of dry dimethylformamide was added. The reaction mixture was heated at 45° C. for an additional 20 minutes and then stirred at ambient temperatures for 1 hour. The mixture was slowly added to 100 ml of water containing two drops of glacial acetic acid. The precipitate was collected by filtration and thoroughly washed with water. The solid was dissolved in methylene chloride and washed with brine and dried with anhydrous sodium sulfate. Evaporation of the solvent afforded 1.11 g of crude product which was purified by column chromatography on silica gel (3g methanol in methylene chloride) to give 0.365 g of 5-Amino-1-[4-(1-naphthoyl)-3,5-dichlorobenzyl]1,2,3-triazole-4-carboxamide and 0.46 g of an isomer of undefined regiochemistry.

EXAMPLE 8

4-[1-(4-Chloro)naphtholy]-3,5-dichlorotoluene

To a cold (-60° C.) stirred solution of 3,5-dichlorotoluene (2.15 g, 13.3 mmol) in 20 ml of dry tetrahydrofuran under a nitrogen atmosphere, a 2.6 M solution of n-butyllithium in hexane (5.37 ml, 14.0 mmol) was added slowly over 10 minutes. The reaction mixture was stirred for an additional 30 minutes at −60° C. and then treated dropwise with a solution of 1-(4-chloro)naphthoyl chloride (3.0 g, 13.3 mmol) in 20 ml of dry tetrahydrofuran over 15 minutes. The reaction mixture was stirred for 4 hours at −60° C. and then quenched with 3.4 ml of saturated NH4Cl solution. The mixture was permitted to come to room temperature at which point it was diluted with 20 ml of water and 20 ml of ether. The layers were separated and the aqueous layer further extracted with ether. The combined extracts were washed with brine, dried with anhydrous magnesium sulfate and concentrated under reduced pressure to give 4.61 g of crude product. This material was chromatographed on silica gel (35:1 hexane:ethyl acetate) to give 0.75 g of pure product.

EXAMPLE 9

4-[1-(4-Chloro)naphthoyl]-3,5-dichlorobenzyl bromide

A warm solution (60° C.) of 4-[1-(4-chloro)naphthoyl]3,5-dichlorotoluene (0.75 g, 2.15 mmol) and dibenzoylperoxide (31 mg, 0.13 mmol) in 30 ml of benzene was treated with N-bromosuccinimide (0.458 g, 2.57 mmol) and then heated at reflux for 17 hours. The reaction mixture was cooled and then diluted with hexane (30 ml) to precipitate succinimide. The precipitate was collected by filtration and thoroughly washed with hexane. The filtrate was concentrated to give 1.04 g of crude product. Chromatography on silica gel (35:1 hexane:ethyl acetate) afforded 0.38 g of pure monobromide product.

EXAMPLE 10

4-[1-(4-Chloro)naphthoyl)-3,5-dichlorobenzyl azide

A solution of 4-[1-(4-chloro)naphthoyl]-3,5-dichlorobenzyl bromide (0.38 g, 0.89 mmol) and tetramethylguanidinium azide (0.253 g, 1.60 mmol) in 40 ml of methylene chloride was heated at reflux for 2 hours. The reaction mixture was diluted with water and the layers separated. The organic layer was washed with brine and dried with anhydrous magnesium sulfate. Concentration afforded 0.39 g of azide

EXAMPLE 11

5-Amino-1-[4-(1-[4-chloro)naphthoyl)-3,5-dichlorobenzyl]-1,2,3-triazole-4-carboxamide A suspension of 2-cyanoacetamide (0.074 g, 0.886 mmol) in 10 ml of ethanol was heated to 60° C. and treated with a 1.23 M methanolic NaOH solution (0.78 ml, 0.957 mmol). The reaction mixture was stirred for 10 minutes and then treated with 0.346 g (0.89 mmol) of 4-(1-(4-chloro)naphthoyl)-3,5-dichlorobenzyl azide. This mixture was stirred at 60° C. for two hours and then cooled. Glacial acetic acid (54 @l) was added followed by 20 ml of water. This aqueous mixture was extracted with methylene chloride. The combined extracts were dried with anhydrous magnesium sulfate and concentrated to afford 0.42 g of crude triazole which was purified by preparative TLC on silica gel (3% methanol in methylene chloride) to give 90 mg of pure triazole.

EXAMPLE 12

1-(4-Chloronaphthalene)methanol

To a solution of 5.0 g (24.2 mmol) of 4-chloro-1-naphthoic in 150 ml of dry tetrahydrofuran (THF), 48 ml of 1M $BH_3$ THF solution was added dropwise over 1 hour. The reaction mixture was stirred for an additional 2.5 hours at room temperature before quenching with aqueous THF (4 ml water in 5 ml THF). The mixture was made alkaline with 10 % sodium carbonate solution and extracted with methylene chloride. The organic extracts were dried with anhydrous magnesium sulfate and concentrated to give 3.0g. This material was chromatographed on silica gel with 3:1 hexane-ethyl acetate as eluant to give 2.0 g of product.

EXAMPLE 13

1-(4-Chloronaphthalene)methyl chloride

A solution of 1.0 g of 1-(4-chloronaphthalene)methanol, 2 ml of thionyl chloride and two drops of N,N-dimethylformamide in 15 ml of methylene chloride was heated at reflux for 2 hours. The reaction mixture was concentrated and the residue redissolved in methylene chloride and washed with 5 % sodium bicarbonate solution and brine. The organic solution was dried with anhydrous magnesium sulfate and concentrated to afford 1.04 g of a solid.

EXAMPLE 14

1-(4-Chloronaphthalene)methyl iodide

A solution of 1-(4-chloronaphthalene)methyl chloride (1.77 g, 8.38 mmol) and sodium iodide (1.71 g, 11.4 mmol) in 20 ml of acetone was stirred at room temperature for 24 hours. The precipitate was filtered and washed with 1:1 hexane-acetone. The filtrate was concentrated and the residue dissolved in ether and washed with water, 5 % $Na_2SO_3$ and brine. The etheral solution was dried with anhydrous magnesium sulfate and concentrated to give 2.33 g of the iodide (Tlc, silical gel 2:1 hexane-ethyl acetate, $R_f$=0.65).

EXAMPLE 15

4-[(4-Chloro-1-naphthalene)methyl]-3,5-dichlorobenzyl Alcohol

To a cold (−60° C.) solution of 3,5-dichlorobenzyl tert-butyldimethylsilyl ether (1.44 g, 4.96 mmol) in 10ml of tetrahydrofuran (THF) under nitrogen, a solution of n-butyl lithium (1.91 ml, 2.6M in hexanes) was slowly added while maintaining the temperature below −50° C.. The solution was stirred for two hours at −60° C. and then treated with a solution of 1-(4-chloronaphthalene)methyl iodide (1.50 g, 4.96 mmol) in 3 ml of THF. The reaction mixture was stirred at −60° C. for 1.5 hours and then permitted to warm to +10° C. over an hour. The reaction mixture was treated with water and 0.6 ml of acetic acid and the resulting mixture extracted with ether. The combined etheral layers were washed with 5 % $NaHCO_3$, brine and dried with anhydrous magnesium sulfate. Concentration gave 2.5 g of crude product which was dissolved in 20 ml of anhydrous THF and treated with 8 ml of a 1M solution of tetra-n-butylammonium fluoride. After 3 hours the reaction mixture was partitioned between water and ether. The etheral layer was washed with brine and then dried with anhydrous magnesium sulfate and concentrated to afford 2.2 g of deprotected product. This material was chromatographed on a silica gel column with methylene chloride as eluent to give 0.58 g of product.

EXAMPLE 16

4-[(4-Chloro-1-naphthalene)methyl]-3,5-dichlorobenzyl azide

4-[(4-Chloro-1-naphthalene)methyl]-3,5-dichlorobenzyl alcohol (0.58 g, 1.65 mmol) in 1 ml of thionyl chloride plus two drops of dimethylformamide were heated at reflux for 2 hours. The reaction mixture was concentrated under reduced pressure and the residue partitioned between ether and 5 % sodium bicarbonate. The etheral layer was further washed with water and brine and then dried with anhydrous magnesium sulfate. Concentration afforded 0.58 g of product. This material was dissolved in 15 ml of methylene chloride and treated with tetramethylguanidinium azide (0.45 g, 2.82 mmol) and sodium iodide (10 mg). The reaction mixture was heated at reflux for 6 hours and then washed with water and brine. The organic phase was dried with anhydrous magnesium sulfate and concentrated to give 0.56 g of product. The crude product was chromatographed on silica gel with 4:1 hexanes-methylene chloride to afford 0.22 g of purified azide.

EXAMPLE 17

5-Amino-1-[4-[(4-chloro-1-naphthalene)methyl]-3,5-dichlorobenzyl]-1,2,3-triazole-4-carboxamide A suspension of 2-cyanoacetamide (49 mg, 0.58 mmol) in 8 ml of absolute ethanol was treated with 0.49 ml of a 1.17 N methanolic sodium hydroxide solution at 40° C. for 10 minutes. To this mixture a solution of 4-[(4-chloro-1-naphthalene) methyl]-3,5-dichlorobenzyl azide (0.22 g, 0.58 mmol) in 2 ml of ethanol was added and the resulting mixture heated at 70° C. for 1.5 hours under nitrogen. The reaction was quenched with 33 @l of acetic acid. Water was added and the reaction mixture extracted with methylene chloride. The combined extracts were washed with brine and then dried with anhydrous magnesium sulfate. Concentration gave 0.26 g of crude product which was purified by preparative TLC on silica gel (3 % methanol in ethyl acetate) to afford 0.20 g of pure triazole.

EXAMPLE 18

4-[(4-Nitro-1-naphthalene)oxy]-3,5-dichlorobenzyl alcohol

A solution of 3,5-dichloro-4-hydroxybenzyl alcohol (1.8 g, 9.3 mmol) in 25 ml of methanol was treated with 0.52 g (9.3 mmol) of KOH. After stirring for 15 minutes, the solution was concentrated under reduced pressure and the residue dissolved in 10 ml of dimethylformamide (DMF). The mixture was heated to 140° C. under nitrogen and treated with a solution of 4-fluoro-1-naphthalene (1.78 g, 9.3 mmol) in 5 ml of DMF. The reaction mixture was heated for 20 minutes and then partitioned between water and methylene chloride. The layers were separated and the aqueous layer further extracted with methylene chloride. The combined extracts were dried with anhydrous magnesium sulfate and concentrated to yield 3 g of crude product. This material was chromatographed on silica el (3:1 hexanes-ethyl acetate) to afford 0.48 g of purified product.

EXAMPLE 19

4-[(4-Chloro-1-naphthalene)oxy]-3,5-dichlorobenzyl alcohol

A solution of 0.9 g (2.47 mmol) of 4-[(4-nitro-1-naphthalene)oxy]-3,5-dichlorobenzyl alcohol, 0.45 g (3 mmol) of tert-butyldimethylsilyl chloride and 0.48 ml of pyridine in 10 ml of dimethylformamide (DMF) under nitrogen was stirred at room temperature overnight. The reaction mixture was partitioned between ether and water. The etheral phase was washed with 1M HCl, water and brine and then dried with anhydrous magnesium sulfate. Evaporation under reduced pressure gave 1.18 g of crude product which was chromatographed on silica gel (2:1 hexanes-methylene chloride) to afford 1.08 g of pure product.

This material was hydrogenated in acetic acid (20 ml) over PtO2 (30 mg) for 40 minutes. The catalysis was removed by filtration and the filtrate concentrated. The residue was dissolved in ether and washed with dilute aqueous ammonia and brine. The etheral layer was dried with anhydrous magnesium sulfate and concentrated to give 0.92 g of crude product which was chromatographed on silica gel with methylene chloride to give 0.56 g of amine product.

To a cold (0° C.) stirred solution of CuCl2 (0.202 g, 1.50 mmol) and isoamylnitrite (0.22 g, 1.88 mmol) in 18 ml of dry acetonitrile under nitrogen, 0.56 g of the above amine was added in 2 ml of acetonitrile and the mixture stirred for two hours at 0° C. before permitting to come to room temperature overnight. The reaction mixture was heated for 1 hour and then partitioned between 20 % HCl and ether. The combined ether extracts were washed with water, dried with anhydrous magnesium sulfate and concentrated to yield 0.51 g of crude product. This material was chromatographed on silica gel (eluted with 3:1 hexanes-methylene chloride then with ethyl acetate) to give 0.06 g of silylated product and 0.086 g of desilylated product. The silylated product was dissolved in 5 ml of dry THF and treated with 0.2 ml of 1M tetra-n-butylammonium fluoride in THF. The reaction mixture was stirred for 2 hours and then partitioned between water and ether. The etheral layer was washed with water and brine and dried with anhydrous magnesium sulfate. Concentration afforded 0.05 g of crude product which was chromatographed on silica gel (3:1 hexanes-ethyl acetate then ethyl acetate) to give 0.04 g of purified desilylated product.

EXAMPLE 20

4-[(4-Chloro-1-naphthalene)oxy]-3,5-dichlorobenzyl azide

A solution of 4-[(4-chloro-1-naphthalene)oxy]3,5-dichlorobenzyl alcohol (0.126 g, 0.35 mmol) in 1 ml of thionyl chloride was heated at reflux under nitrogen for 1 hour. The mixture was concentrated under reduced pressure and the residue dissolved in ether and washed with 5 % NaHCO3 solution, water and brine. The etheral layer was dried with anhydrous magnesium sulfate and concentrated to give 0.126 g of benzyl chloride product.

This chloride was dissolved in 5 ml of methylene chloride and treated with 94 mg (0.59 mmol) of tetramethylguanidinium azide and 2 mg of sodium iodide. The reaction mixture was heated overnight at reflux and then washed with water and brine. The organic solution was then dried with anhydrous magnesium sulfate and concentrated to yield 0.12 g of crude azide. This material was purified by preparative TLC (2:1 hexanes-methylene chloride) to give 112 mg of purified product.

EXAMPLE 21

5-Amino-1-[4-[(4-chloro-1-naphthalene)oxy]-3,5-dichlorobenzyl]-1,2,3-triazole-4-carboxamide A suspension of 2-cyanoacetamide (26 mg, 0.304 mmol) in 5 ml of ethanol is treated with 0.234 ml of 1.3M methanolic NaOH solution. The solution was heated at 40° C. for 10 minutes under nitrogen and then treated with 112 mg (0.304 mmol) of 4-[(4-chloro-1-naphthalene)oxy]-3,5-dichlorobenzyl azide. The reaction mixture was stirred for 1 hour at reflux and then quenched with 30 @; of glacial acetic acid, diluted with 25 ml of water and extracted with methylene chloride. The combined extracts were dried with anhydrous magnesium sulfate and concentrated to afford 135 mg of crude product which was purified by preparative TLC (3% methanol/ethyl acetate) to give 117 mg of pure triazole.

EXAMPLE 22

4-[1-(4-Fluoro)naphthoyl]-3,5-dichlorobenzyl alcohol

To a cold (-60° C.) solution of 3,5-dichlorobenzyl tert-butyldimethylsilyl ether (1.5 g) in 10 ml of anhydrous tetrahydrofuran under nitrogen, 2ml of 2.6M n-butyl lithium in hexanes is slowly added (T< −50° C.). The solution is stirred at −60° C. for two hours and then treated with a solution of 1-(4-fluoro)naphthoyl) chloride (1.5 g) in tetrahydrofuran (3 ml). The reaction mixture is stirred for 2 hours at -60° C. and then permitted to warm to room temperature. The reaction is quenched with acetic acid and water and the resulting mixture extracted repeatedly with ether. The combined etheral layers are washed with sodium bicarbonate solution and brine and then dried with anhydrous magnesium sulfate. The solution is concentrated and the residue redissolved in tetrahydrofuran (20 ml) and treated with 10 ml of 1M tetra-n-butylammonium fluoride in tetrahydrofuran. The reaction mixture is stirred for 5 hours and then partitioned between ether and water. The ethereal layer is washed with brine, dried with anhydrous magnesium sulfate and then concentrated to dryness. The residue is chromatographed on silica gel to afford the desired product.

EXAMPLE 23

4-[1-(4-Fluoro)naphthoyl]-3,5-dichlorobenzyl azide

A solution of 1 g of 4-[1-(4-fluoro)naphthoyl]-3,5dichlorobenzyl alcohol in 2 ml of thionyl chloride containing two drops of N,N-dimethylformamide is heated at reflux for 3 hours and then concentrated under reduced pressure. The residue is dissolved in ether and washed with 5 % sodium bicarbonate solution, water and brine and then dried with anhydrous magnesium sulfate. The etheral solution was concentrated. The residue is then dissolved in ethanol (15 ml), treated with sodium azide (0.6 g) and the resulting mixture heated at reflux for 5 hours. The reaction mixture is then concentrated and partitioned between water and ether. The etheral extracts is dried with anhydrous magnesium sulfate and concentrated. The crude product is chromatographed on silica gel to give pure azide.

5-Amino-1-[4-(1-(4-fluoro)naphthoyl)-3,5-dichlorobenzyl]1,2,3-triazole-4-carboxamide A suspension of 2-cyanoacetamide (0.15 g) in 20 ml of ethanol is heated to 60° C. and treated with 1.1 equivalents of methanolic sodium hydroxide solution. The reaction mixture is stirred for 10 minutes and then treated with 0.7 g of 4-[1-(4-fluoro)naphthoyl]3,5-dichlorobenzyl azide. The mixture is stirred for approximately two hours at 60° C. and then quenched with acetic acid. The reaction mixture is added to water and then extracted repeatedly with methylene chloride. The combined extracts are dried with anhydrous magnesium sulfate and then concentrated. The crude product is chromatographed on silica gel to afford pure triazole.

EXAMPLE 25

4-[1-(4-Bromo)naphthoyl]-3,5-dichlorobenzyl alcohol

To a cold (−60° C.) solution of 3,5-dichlorobenzyl tert-butyldimethylsilyl ether (0.7 g) in 5 ml of anhydrous tetrahydrofuran under nitrogen, 1 ml of 2.6M n-butyl lithium in hexanes is slowly added (T< −50° C.). The solution is stirred at −60° C. for two hours and then treated with a solution of 1-(4-bromo)naphthoyl) chloride (0.75 g) in tetrahydrofuran (2 ml). The reaction mixture is stirred for 2 hours at −60° C. and then permitted to warm to room temperature. The reaction is quenched with acetic acid and water and the resulting mixture extracted repeatedly with ether. The combined etheral layers are washed with sodium bicarbonate solution and brine and then dried with anhydrous magnesium sulfate. The solution is concentrated and the residue redissolved in tetrahydrofuran (10 ml) and treated with 5 ml of 1M tetra-n-butylammonium fluoride in tetrahydrofuran. The reaction mixture is stirred for 5 hours and then partitioned between ether and water. The ethereal layer is washed with brine, dried with anhydrous magnesium sulfate and then concentrated to dryness. The residue can be chromatographed on silica gel to afford the desired product.

EXAMPLE 26

4-[1-(4-Bromo)naphthoyl]-3,5-dichlorobenzyl azide

A solution of 0.5g of 4-[1-(4-bromo)naphthoyl]-3,5dichlorobenzyl alcohol in 2 ml of thionyl chloride containing two drops of N,N-dimethylformamide is heated at reflux for 3 hours and then concentrated under reduced pressure. The residue is dissolved in ether and washed with 5 % sodium bicarbonate solution, water and brine and then dried with anhydrous magnesium sulfate. The etheral solution is concentrated. The residue is then dissolved in ethanol (15 ml), treated with sodium azide (0.6 g) and the resulting mixture heated at reflux for 5 hours. The reaction mixture is then concentrated and partitioned between water and ether. The etheral extracts is dried with anhydrous magnesium sulfate and concentrated. The crude product is chromatographed on silica gel to yield pure azide.

EXAMPLE 27

5-Amino-1-[4-(1-(4-bromo)naphthoyl)-3,5-dichlorobenzyl]-1,2,3-triazole-4-carboxamide A suspension of 2-cyanoacetamide (0.075 g) in 10 ml of ethanol is heated to 60° C. and treated with 1.1 equivalents of methanolic sodium hydroxide solution. The reaction mixture is stirred for 10minutes and then treated with 0.35 g of 4-[1-(4-bromo)naphthoyl]3,5-dichlorobenzyl azide. The mixture is stirred for approximately two hours at 60° C. and then quenched with acetic acid. The reaction mixture is added to water and then extracted repeatedly with methylene chloride. The combined extracts are dried with anhydrous magnesium sulfate and then concentrated. The crude product is chromatographed on silica gel to afford pure triazole.

EXAMPLE 28

4-[2-(6-Chloro)naphthoyl]-3,5-dichlorobenzyl alcohol

To a cold (−60° C.) solution of 3,5-dichlorobenzyl tert-butyldimethylsilyl ether (1.5 g) in 10 ml of anhydrous tetrahydrofuran under nitrogen, 2ml of 2.6M n-butyl lithium in hexanes is slowly added (T< −50° C.). The solution is stirred at −60° C. for two hours and then treated with a solution of 2-(6-chloro)naphthoyl) chloride (1.5 g) in tetrahydrofuran (3 ml). The reaction mixture is stirred for 2 hours at −60° C. and then permitted to warm to room temperature. The reaction is quenched with acetic acid and water and the resulting mixture extracted repeatedly with ether. The combined etheral layers are washed with sodium bicarbonate solution and brine and then dried with anhydrous magnesium sulfate. The solution is concentrated and the residue redissolved in tetrahydrofuran (20 ml) and treated with 10 ml of 1M tetra-n-butylammonium fluoride in tetrahydrofuran. The reaction mixture is stirred for 5 hours and then partitioned between ether and water. The ethereal layer is washed with brine, dried with anhydrous magnesium sulfate and then concentrated to dryness. The residue is chromatographed on silica gel to afford the desired product.

EXAMPLE 29

4-[2-(6-Chloro)naphthoyl]-3,5-dichlorobenzyl azide

A solution of 1 g of 4-[2-(6-chloro)naphthoyl]-3,5dichlorobenzyl alcohol in 2 ml of thionyl chloride containing two drops of N,N-dimethylformamide is heated at reflux for 3 hours and then concentrated under reduced pressure. The residue is dissolved in ether and washed with 5 % sodium bicarbonate solution, water and brine and then dried with anhydrous magnesium sulfate. The etheral solution was concentrated. The residue is then dissolved in methylene chloride (150 ml), treated with tetramethylguanidinium azide (0.66 g) and the resulting mixture heated at reflux for 5 hours. The reaction mixture is diluted with water and the layers separated. The organic layer is washed with brine and dried with anhydrous magnesium sulfate. The solution is concentrated and the crude product is chromatographed on silica gel to give pure azide.

EXAMPLE 30

5-Amino-1-[4-(2-(6-chloro)naphthoyl)-3,5-dichlorobenzyl]-1,2,3-triazole-4-carboxamide A suspension of 2-cyanoacetamide (0.15 g) in 20 ml of ethanol is heated to 60° C. and treated with 1.1 equivalents of methanolic sodium hydroxide solution. The reaction mixture is stirred for 10 minutes and then treated with 0.7 g of 4-[2-(6-chloro)naphthoyl]3,5-dichlorobenzyl azide. The mixture is stirred for approximately two hours at 60° C. and then quenched with acetic acid. The reaction mixture is added to water and then extracted repeatedly with methylene chloride. The combined extracts are dried with anhydrous magnesium sulfate and then concentrated. The crude product is chromatographed on silica gel to afford pure triazole.

EXAMPLE 31

4-(1-Naphthoyl)-3,5-dimethylbenzyl bromide

A warm solution (60° C.) of 4-(1-naphthyl)-2,4,6trimethylphenyl)ketone (1.30 g) and dibenzoylperoxide (72 mg) in 50 ml of benzene is treated with N-bromosuccinimide (1.06 g) and then heated at reflux for 24 hours. The reaction mixture is cooled and diluted with hexanes to precipitate succinimide. The precipitate is collected by filtration and thoroughly washed with 70:30 methylene chloride:ethyl acetate. The filtrate is concentrated to give a crude mixture of mono- and dibromides. The desired symmetrical monobromide can be isolated by chromatography.

EXAMPLE 32

5-Amino-1-[4-(1-naphthoyl)-3,5-dimethylbenzyl]-1,2,3-triazole-4-carboxamide

A solution of 5-amino-1,2,3-triazole-4-carboxamide (182 mg, 1.43 mmol) in 5 ml of dry dimethylformamide (DMF) is treated with 50% sodium hydride dispersion in mineral oil (70mg). The reaction mixture is warmed to 45° C. and stirred for 1 hour. To this mixture, a solution of 4-(1-naphthoyl)-3,5dimethylbenzyl bromide (0.43 g, 1.2 mmol) in 5 ml of dry DMF is added. The reaction mixture is stirred at 45° C. for an additional 20 minutes and then stirred at room temperature for 1 hour. The reaction mixture is added slowly to water containing a small quantity of glacial acetic acid. The mixture is extracted with methylene chloride and the combined extracts washed with brine and dried with anhydrous sodium sulfate. Solvent is removed and the crude mixture of two triazoles is chromatographed on silica gel to give the titled compound.

EXAMPLE 33

3,5-Dichloro-4-[(1-naphthyl)thio]benzene carboxamide

To a solution of 3,4,5-trichlorobenzene carboxamide (25 g) in 220 ml of dry dimethylformamide (DMF), 26 g of 1-naphthalenethiol potassium salt is added and the reaction mixture stirred at room temperature for two days. The reaction mixture is then diluted with water and extracted with methylene chloride. The combined extracts are washed with water, dried with anhydrous magnesium sulfate and concentrated. The product can be purified by chromatography on silica gel.

EXAMPLE 34

3,5-Dichloro-4-[(1-naphthyl)thio]benzyl amine

A solution of 25 g of 3,5-dichloro-4-[(1-naphthyl)thio]benzene carboxamide in 150 ml of dry tetrahydrofuran (THF) is treated with 230 ml of 1.0 M BH$_3$-THF complex. The resulting solution is heated at reflux for 16 hours. The reaction mixture is cooled with ice and quenched with excess 2 N HCl. The mixture is then made basic with NaOH and extracted with methylene chloride. The combined extracts are washed with water and dried with anhydrous magnesium sulfate. Concentration under reduced pressure affords the crude product which is purified by column chromatography on silica gel.

EXAMPLE 35

3,5-Dichloro-4-[(1-naphthyl)thio]benzyl azide

To a solution of 3.59 g of 3,5-dichloro-4-[(1-naphthyl)thio]benzyl amine in 30 ml of absolute ethanol, 3.5 g of 2,4,6-triphenylpyrylium tetrafluoroborate is added and the reaction mixture is stirred overnight at room temperature. Ether is added to complete the precipitation. The solid is collected and then dissolved in 25 ml of dry DMF and treated with 2.3 g of sodium azide. The reaction mixture is then heated at 130° C. for 8 hours, diluted with 250 ml of water and repeatedly extracted with ether. The combined extracts are washed with water and dried. Concentration and chromatography on silica gel will provide pure azide.

EXAMPLE 36

5-Amino-1-[(3,5-dichloro-4-(1-naphthyl)thio)benzyl]1,2,3-triazole-4-carboxamide

A suspension of anhydrous, powdered potassium carbonate (1.2 g) and cyanoacetamide (0.2 g) in DMSO (5 ml) is stirred for 30 minutes at room temperature and then treated with 0.8 g of 3,5-dichloro-4-[(1-naphthyl)thio]benzyl azide. The mixture is stirred at room temperature for 16 hours. The solids are removed by filtration and the filtrate diluted with water. The aqueous mixture is repeatedly extracted with methylene chloride. The organic extracts are backwashed with water and dried with anhydrous magnesium sulfate. The mixture is concentrated and the product purified by either chromatography or recrystallization from an appropriate solvent.

EXAMPLE 36

Using essentially the same chemistry and procedures described in Examples 22–24 and 18–21, the following analogs are prepared from readily available starting materials:

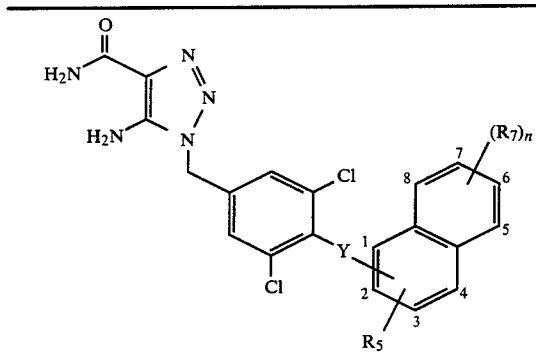

| $R_5$ | Y | n | $R_7$ |
|---|---|---|---|
| H | 1-CO | 1 | 6-Cl |
| H | 1-CH$_2$ | 1 | 6-F |
| H | 1-CO | 1 | 6-Br |
| H | 1-CO | 1 | 8-Br |
| 4-F | 1-O | 0 | |
| 4-Br | 1-O | 0 | |
| H | 1-CO | 1 | 6-OCH$_3$ |
| 4-OCH$_3$ | 1-CH$_2$ | 0 | |
| H | 2-CO | 3 | 4,5,6-trimethoxy |
| 4-F | 1-CH$_2$ | 0 | |
| 4-CF$_3$ | 1-CO | 0 | |
| 4-I | 1-CO | 0 | |
| 4-(C(Cl)=C(Cl)2) | 1-CO | 0 | |
| 5-F | 1-CH$_2$ | 0 | |
| 3-Cl | 1-CO | 0 | |
| 3-F | 2-CO | 0 | |
| 2-CH$_3$ | 1-CH$_2$ | 0 | | when n = 0, R$_7$ is H.

What is claimed is:

1. A pharmaceutical composition for controlling, hyperliferation in mammalian cells comprising a pharmaceutical carrier and a therapeutically effective amount of a compound of formula

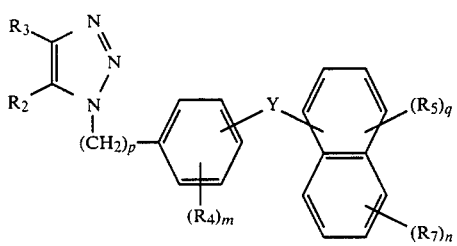

wherein
p is 0 to 2;
m and n independently are 0 to 4;
q is 0 to 3;
Y is O, S, SO, SO$_2$, CO, CHCN, CHF, CH$_2$, or C=NR$_6$ where R$_6$ represents
 (a) hydrogen;
 (b) loweralkyl;
 (c) hydroxy;
 (d) loweralkoxy;
 (e) amino;
 (f) loweralkylamino;
 (g) diloweralkylamino; or
 (h) cyano;
R$_4$, R$_5$ and R$_7$ independently are
 (a) halogen;
 (b) cyano;
 (c) trifluoromethyl;
 (d) loweralkanoyl;
 (e) nitro;
 (f) loweralkyl;
 (g) loweralkoxy;
 (h) carboxy;
 (i) carbaloxy;
 (j) trifluoromethoxy;
 (k) acetamido;
 (l) loweralkylthio;
 (m) loweralkylsulfonyl;
 (n) loweralkylsulfonyl;
 (o) trichlorovinyl;
 (p) trifluoromethylthio;
 (q) trifluoromethylsulfinyl; or
 (r) trifluoromethylsulfonyl;
R$_2$ is
 (a) amino;
 (b) mono or diloweralkylamino;
 (c) acetamido;
 (d) acetimido;
 (e) ureido;
 (f) formamido;
 (g) formimido; or
 (h) guanidino; and
R$_3$ is
 (a) carbamoyl;
 (b) cyano;
 (c) carbazoyl;
 (d) carbazoyl;
 (e) amidino; or
 (f) N-hydroxycarbamoyl.

2. The composition of claim 1 wherein n m, and q independently are 0, 1 or 2; p is 1; Y is O, S, CO, or CH$_2$; R$_4$ is
 (a) fluoro;
 (b) chloro;
 (c) bromo;
 (d) methyl;
 (e) trifluoromethyl;
 (f) cyano;
 (g) carbomethoxy;
 (h) trifluoromethoxy;
 (i) trifluoromethylthio;
 (j) nitro; or
 (k) trichlorovinyl;
R$_5$ and R$_7$ independently are
 (a) chloro;
 (b) bromo;
 (c) fluoro;
 (d) methyl;
 (e) trifluoromethyl;
 (f) cyano;
 (g) carbalkoxy;
 (h) trichlorovinyl;
 (i) nitro.

(j) trifluoromethyoxy; or
(k) trifluoromethylthio.

3. The composition of claim 1 wherein
p is 1;
$R^4$ is chloro or fluoro;
m is 0, 1 or 2; n and q independently are 0 or 1; and
$R_5$ and $R_7$ independently are chloro or fluoro.

4. The composition of claim 1 wherein the compound is 5-amino-1(4-[4-chloronaphthoyl]-3,5-dichlorobenzyl)-1,2,3-triazole-4-carboxamide.

5. A compound of formula

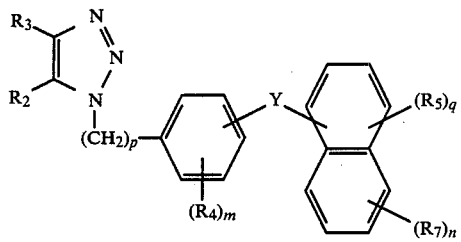

(I)

wherein
p is 0 to 2;
m and n independently are 0 to 4;
q is 0 to 3;
Y is O, S, SO, $SO_2$, CO, CHCN, CHF, $CH_2$, or C=$NR_6$
where $R_6$ represents
 (a) hydrogen;
 (b) loweralkyl;
 (c) hydroxy;
 (d) loweralkoxy;
 (e) amino;
 (f) loweralkylamino;
 (g) diloweralkylamino; or
 (h) cyano;
$R_4$, $R_5$ and $R_7$ independently are
 (a) halogen;
 (b) cyano;
 (c) trifluoromethyl;
 (d) loweralkanoyl;
 (e) nitro;
 (f) loweralkyl;
 (g) loweralkoxy;
 (h) carboxy;
 (i) carbaloxy;
 (j) trifluoromethoxy;
 (k) acetamido;
 (l) loweralkylthio;
 (m) loweralkylsulfonyl;
 (n) loweralkylsulfonyl;
 (o) trichlorovinyl;
 (p) trifluoromethylthio;
 (q) trifluoromethylsulfinyl; or
 (r) trifluoromethylsulfonyl;
$R_2$ is
 (a) amino;
 (b) mono or diloweralkylamino;
 (c) acetamido;
 (d) acetimido;
 (e) ureido;
 (f) formamido;
 (g) formimido; or
 (h) guanidino; and
$R_3$ is
 (a) carbamoyl;
 (b) cyano;
 (c) carbazoyl;
 (d) carbazoyl;
 (e) amidino; or
 (f) N-hydroxycarbamoyl.

6. The compound of claim 9 wherein
$R_4$ is
 (a) fluoro;
 (b) chloro;
 (c) bromo;
 (d) methyl;
 (e) trifluoromethyl;
 (f) cyano;
 (g) carbomethoxy;
 (h) trifluoromethoxy;
 (i) trifluoromethylthio;
 (j) nitro; or
 (k) trichlorovinyl;
$R_5$ and $R_7$ independently are
 (a) chloro;
 (b) bromo;
 (c) fluoro;
 (d) methyl;
 (e) trifluoromethyl;
 (f) cyano;
 (g) carbalkoxy;
 (h) trichlorovinyl;
 (i) nitro.
 (j) trifluoromethyoxy; or
 (k) trifluoromethylthio.

7. The compound of claim 9 wherein
p is 1;
$R^4$ is chloro or fluoro;
m is 0, 1 or 2;
n and q independently 0 or 1; and
$R_5$ and $R_7$ independently are chloro or fluoro.

8. The compound of claim 9 which is the compound is 5-amino-1-(4-[4-chloronaphthoyl]-3,5-dichlorobenzyl)-1,2,3-triazole-4-carboxamide.

* * * * *